United States Patent
Dudley, Jr. et al.

(10) Patent No.: US 7,550,299 B2
(45) Date of Patent: Jun. 23, 2009

(54) METHOD FOR PREDICTING ONSET/RISK OF ATRIAL FIBRILLATION (AF)

(75) Inventors: Samuel C. Dudley, Jr., Atlanta, GA (US); Dean P. Jones, Decatur, GA (US)

(73) Assignees: The United States of America as represented by the Department of Veterans Affairs, Washington, DC (US); Emory University, Atlanta, GA (US)

(*) Notice: Subject to any disclaimer, the term of this patent is extended or adjusted under 35 U.S.C. 154(b) by 0 days.

(21) Appl. No.: 11/882,627

(22) Filed: Aug. 3, 2007

(65) Prior Publication Data
US 2008/0033258 A1 Feb. 7, 2008

Related U.S. Application Data

(60) Provisional application No. 60/835,074, filed on Aug. 3, 2006.

(51) Int. Cl.
*G01N 33/00* (2006.01)
*G01N 33/48* (2006.01)

(52) U.S. Cl. .................. 436/86; 436/63; 600/300; 128/898

(58) Field of Classification Search .......... 436/63, 436/86, 119; 600/300; 128/898
See application file for complete search history.

(56) References Cited

U.S. PATENT DOCUMENTS

2005/0112572 A1* 5/2005 Pincemail et al. .......... 435/6
2005/0202521 A1* 9/2005 Crum .......................... 435/26

FOREIGN PATENT DOCUMENTS

WO 2005/016216 * 2/2005

OTHER PUBLICATIONS

Kim, Young Hoon et al. Gene Expression Profiling of Oxidative Stress on Atrial Fibrillation in Humans. Experimental and Molecular Medicine, vol. 35, No. 5, pp. 336-349, Oct. 2003.*
Abramson, J. L.; Hooper, W. C.; Jones, D. P.; Ashfaq, S.; Rhodes, S. D.; Weintraub, W. S.; Harrison, D. G.; Quyyumi, A. A.; Vaccarino, V. Association between novel oxidative stress markers and C-reactive protein among adults without clinical coronary heart disease. *Atherosclerosis* 178:115-121; 2005.
Amar, D.; Zhang, H.; Heerdt, P. M.; Park, B.; Fleisher, M.; Thaler. H. T. Statin use is associated with a reduction in atrial fibrillation after noncardiac thoracic surgery independent of C-reactive protein. *Chest* 128:3421-3427; 2005.
Aviles, R. J.; Martin, D. O.; Apperson-Hansen, C.; Houghtaling, P. L.; Rautaharju, P.; Kronmal, R. A.; Tracy, R. P.; Van Wagoner, D. R.; Psaty, B. M.; Lauer, M. S.; Chung, M. K. Inflammation as a risk factor for atrial fibrillation. *Circulation* 108:3006-3010; 2003.

(Continued)

*Primary Examiner*—Maureen M Wallenhorst
(74) *Attorney, Agent, or Firm*—Dinesh Agarwal, P.C.

(57) ABSTRACT

A method for predicting onset or risk of atrial fibrillation in a subject includes determining the presence of an oxidative stress marker, such as glutathione, cysteine, and/or a derivative of a reactive oxidative metabolite (DROM).

15 Claims, 4 Drawing Sheets

OTHER PUBLICATIONS

Barrington, P. L.; Martin, R. L.; Zhang, K. Slowly inactivating sodium currents are reduced by exposure to oxidative stress. *J Mol Cell Cardiol* 29:3251-3265; 1997.

Benjamin, E. J.; Levy, D.; Vaziri, S. M.; D'Agostino, R. B.; Belanger, A. J.; Wolf, P. A. Independent risk factors for atrial fibrillation in a population-based cohort. The Framingham Heart Study. *JAMA* 271:840-844; 1994.

Boos, C. J.; Anderson, R. A.; Lip, G. Y. Is atrial fibrillation an inflammatory disorder? *Eur Heart J* 27:136-149; 2006.

Braunwald, E. Shattuck lecture—cardiovascular medicine at the turn of the millennium: triumphs, concerns, and opportunities. *N Engl J Med* 337:1360-1369; 1997.

Bruins, P.; te, V. H.; Yazdanbakhsh, A. P.; Jansen, P. G.; van Hardevelt, F. W.; de Beaumont, E. M.; Wildevuur, C. R.; Eijsman, L.; Trouwborst, A.; Hack, C. E. Activation of the complement system during and after cardiopulmonary bypass surgery: postsurgery activation involves C-reactive protein and is associated with postoperative arrhythmia. *Circulation* 96:3542-3548; 1997.

Cai, H.; Li, Z.; Goette, A.; Mera, F.; Honeycutt, C.; Feterik, K.; Wilcox, J. N.; Dudley, S. C., Jr.; Harrison, D. G.; Langberg, J. J. Downregulation of endocardial nitric oxide synthase expression and nitric oxide production in atrial fibrillation: potential mechanisms for atrial thrombosis and stroke. *Circulation* 106:2854-2858; 2002.

Calo, L.; Bianconi, L.; Colivicchi, F.; Lamberti, F.; Loricchio, M. L.; de Ruvo, E.; Meo, A.; Pandozi, C.; Staibano, M.; Santini, M. N-3 Fatty acids for the prevention of atrial fibrillation after coronary artery bypass surgery: a randomized, controlled trial. *J Am Coll Cardiol* 45:1723-1728; 2005.

Carnes, C. A.; Chung, M. K.; Nakayama, T.; Nakayama, H.; Baliga, R. S.; Piao, S.; Kanderian, A.; Pavia, S.; Hamlin, R. L.; McCarthy, P. M.; Bauer, J. A.; Van Wagoner, D. R. Ascorbate attenuates atrial pacing-induced peroxynitrite formation and electrical remodeling and decreases the incidence of postoperative atrial fibrillation. *Circ Res* 89:E32-E38; 2001.

Cesarone, M. R.; Belcaro, G.; Carratelli, M.; Cornelli, U.; De Sanctis, M. T.; Incandela, L.; Barsotti, A.; Terranova, R.; Nicolaides, A. A simple test to monitor oxidative stress. *Int Angiol* 18:127-130; 1999.

Choudhary, G.; Dudley, S. C., Jr. Heart failure, oxidative stress, and ion channel modulation. *Congest Heart Fail* 8:148-155; 2002.

Christ, M.; Bauersachs, J.; Liebetrau, C.; Heck, M.; Gunther, A.; Wehling, M. Glucose increases endothelial-dependent superoxide formation in coronary arteries by NAD(P)H oxidase activation: attenuation by the 3-hydroxy-3-methylglutaryl coenzyme A reductase inhibitor atorvastatin. *Diabetes* 51:2648-2652: 2002.

Chung, M. K.; Martin, D. O.; Sprecher, D.; Wazni, O.; Kanderian, A.; Carnes, C. A.; Bauer, J. A.; Tchou, P. J.; Niebauer, M. J.; Natale, A.; Van Wagoner, D. R. C-reactive protein elevation in patients with atrial arrhythmias: inflammatory mechanisms and persistence of atrial fibrillation. *Circulation* 104:2886-2891: 2001.

Ciaroni, S.; Cuenoud, L.; Bloch, A. Clinical study to investigate the predictive parameters for the onset of atrial fibrillation in patients with essential hypertension. *Am Heart J* 139:814-819; 2000.

Conway, D. S.; Buggins, P.; Hughes, E.; Lip, G. Y. Relationship of interleukin-6 and C-reactive protein to the prothrombotic state in chronic atrial fibrillation. *J Am Coll Cardiol* 43:2075-2085; 2004.

Cornelli, U.; Terranova, R.; Luca, S.; Cornelli, M.; Alberti, A. Bioavailability and antioxidant activity of some food supplements in men and women using the D-Roms test as a marker of oxidative stress. *J Nutr* 131:3208-3211; 2001.

De Vecchi, E.; Pala, M. G.; Di Credico, G.; Agape, V.; Paolini, G.; Bonini, P. A.; Grossi, A.; Paroni, R. Relation between left ventricular function and oxidative stress in patients undergoing bypass surgery. *Heart* 79:242-247; 1998.

Dernellis, J.; Panaretou, M. C-reactive protein and paroxysmal atrial fibrillation: evidence of the implication of an inflammatory process in paroxysmal atrial fibrillation. *Acta Cardiol* 56:375-380; 2001.

Dernellis, J.; Panaretou, M. Relationship between C-reactive protein concentrations during glucocorticoid therapy and recurrent atrial fibrillation. *Eur Heart J* 25:1100-1107; 2004.

Dernellis, J.; Panaretou, M. Effect of C-reactive protein reduction on paroxysmal atrial fibrillation. *Am Heart J* 150:1064; 2005.

Dudley, S. C., Jr.; Diamandopoulus, L.; Dikalov, S.; Fink, B.; Fink, N.; McCann, L.; Honeycutt, C.; Mera, F.; Harrison, D. G.; Langberg, J. J. Atrial fibrillation causes increased oxidative stress and decreased nitric oxide bioavailability in the left atrial appendage. Circulation 108:IV-147-IV-148. (2003).

Dudley, S. C., Jr.; Hoch, N. E.; McCann, L. A.; Honeycutt, C.; Diamandopoulus, L.; Fukai, T.; Harrison, D. G.; Langberg, J. Atrial fibrillation increases production of superoxide by the left atrium and left atrial appendage: role of the NADPH and xanthine oxidases. *Circulation* 112:1266-1273; 2005.

Durak, I.; Elgun, S.; Kemal, B. N.; Burak Cimen, M. Y.; Kacmaz, M.; Buyukkocak, S.; Serdar, O. H. Effects of cigarette smoking with different tar content on erythrocyte oxidant/antioxidant status. *Addiction Biology* 7:255-258; 2002.

Falk, R. H. Impacts of prospective peer review on pacemaker implantation rates in Massachusetts. *J Am Coll Cardiol* 15:1087-1092; 1990.

Feinberg, W. M.; Blackshear, J. L.; Laupacis, A.; Kronmal, R.; Hart, R. G. Prevalence, age distribution, and gender of patients with atrial fibrillation. Analysis and implications. *Arch Intern Med* 155:469-473; 1995.

Fontes, M. L.; Mathew, J. P.; Rinder, H. M.; Zelterman, D.; Smith, B. R.; Rinder, C. S. Atrial fibrillation after cardiac surgery/cardiopulmonary bypass is associated with monocyte activation. *Anesth Analg* 101:17-23, table; 2005.

Frustaci, A.; Chimenti, C.; Bellocci, F.; Morgante, E.; Russo, M. A.; Maseri, A. Histological substrate of atrial biopsies in patients with lone atrial fibrillation. *Circulation* 96:1180-1184; 1997.

Fukuda, K.; Davies, S. S.; Nakajima, T.; Ong, B. H.; Kupershmidt, S.; Fessel, J.; Amarnath, V.; Anderson, M. E.; Boyden, P. A.; Viswanathan, P. C.; Roberts, L. J.; Balser, J. R. Oxidative mediated lipid peroxidation recapitulates proarrhythmic effects on cardiac sodium channels. *Circ Res* 97:1262-1269; 2005.

Furberg, C. D.; Psaty, B. M.; Manolio, T. A.; Gardin, J. M.; Smith, V. E.; Rautaharju, P. M. Prevalence of atrial fibrillation in elderly subjects (the Cardiovascular Health Study). *Am J Cardiol* 74:236-241; 1994.

Ganter, U.; Arcone, R.; Toniatti, C.; Morrone, G.; Ciliberto, G. Dual control of C-reactive protein gene expression by interleukin-1 and interleukin-6. *EMBO J* 8:3773-3779; 1989.

Gaudino, M.; Andreotti, F.; Zamparelli, R.; Di Castelnuovo, A.; Nasso, G.; Burzotta, F.; Iacoviello, L.; Donati, M. B.; Schiavello, R.; Maseri, A.; Possati, G. The -174G/C interleukin-6 polymorphism influences postoperative interleukin-6 levels and postoperative atrial fibrillation. Is atrial fibrillation influences inflammatory complication? *Circulation* 108 Suppl 1:II195-II199; 2003.

Goette, A.; Juenemann, G.; Peters, B.; Klein, H. U.; Roessner, A.; Huth, C.; Rocken, C. Determinants and consequences of atrial fibrosis in patients undergoing open heart surgery. *Cardiovasc Res* 54:390-396; 2002.

Guazzi, M.; Belletti, S.; Bianco, E.; Lenatti, L.; Maurizio, G. D. Endothelial dysfunction and exercise performance in lone atrial fibrillation or associated with hypertension or diabetes. Different results with cardioversion. *Am J physiol* 2006.

Hart, R. G.; Halperin, J. L. Atrial fibrillation and stroke: concepts and controversies. *Stroke* 32:803-808; 2001.

Heymes, C.; Bendall, J. K.; Ratajczak, P.; Cave, A. C.; Samuel, J. L.; Hasenfuss, G.; Shah, A. M. Increased myocardial NADPH oxidase activity in human heart failure. *J Am Coll Cardiol* 41:2164-2171; 2003.

Incandela, L.; Belcaro, G.; Cesarone, M. R.; De sanctis, M. T.; Griffin, M.; Cacchio, M.; Nicolaides, A. N.; Bucci, M.; Barsotti, A.; Martines, G.; Cornelli, U.; Di Renzo, A. Oxygen-free radical decrease in hypertensive patients treated with lercanidipine. *Int Angiol* 20:136-140; 2001.

Ishida, K.; Kimura, F.; Imamaki, M.; Ishida, A.; Shimura, H.; Kohno, H.; Sakurai, M.; Miyazaki, M. Relation of inflammatory cytokines to atrial fibrillation after off-pump coronary artery bypass grafting. *Eur J Cardiothoracic Surg* 29:501-505; 2006.

Ishii, Y.; Schuessler, R. B.; Gaynor, S. L.; Yamada, K.; Fu, A. S.; Boineau, J. P.; Damiano, R. J., Jr. Inflammation of atrium after cardiac surgery is associated with inhomogeneity of atrial conduction and atrial fibrillation. *Circulation* 111:2881-2888; 2005.

Jonas, C. R.; Puckett, A. B.; Jones, D. P.; Szeszycki, E. E.; Bergman, G. F.; Furr, C. E.; Tyre, C.; Carlson, J. L.; Galloway, J. R.; Blumberg, J. B.; Ziegler, T. R. Plasma antioxidant status after high-dose chemotherapy: a randomized trial of parenteral nutrition in bone marrow transplantation patients. *Am J Clin Nutr* 72:181-189; 2000.

Jones, D. P. Redox potential of GSH/GSSG couple: assay and biological significance. *Methods Enzymol* 348:93-112; 2002.

Jones, D. P.; Carlson, J. L.; Samiec, P. S.; Sternberg, P., Jr.; Mody, V. C., Jr.; Reed, R. L.; Brown, L. A. Glutathione measurement in human plasma. Evaluation of sample collection, storage and derivatization conditions for analysis of dansyl derivatives by HPLC. *Clin Chim Acta* 275:175-184; 1998.

Jones, D. P.; Mody, V. C., Jr.; Carlson, J. L.; Lynn, M. J.; Sternberg, P., Jr. Redox analysis of human plasma allows separation of pro-oxidant events of aging from decline in antioxidant defenses. *Free Radic Biol Med* 33:1290-1300; 2002.

Kannel, W. B.; Wolf, P. A.; Benjamin, E. J.; Levy, D. Prevalence, incidence, prognosis, and predisposing conditions for atrial fibrillation: population-based estimates. *Am J Cardiol* 82:2N-9N; 1998.

Khairallah, F.; Ezzedine, R.; Ganz, L. I.; London, B.; Saba, S. Epidemiology and determinants of outcome of admissions for atrial febrillation in the United States from 1996 to 2001. *Am J Cardiol* 94:500-504; 2004.

Kim, Y. M.; Guzik, T. J.; Zhang, Y. H.; Zhang, M. H.; Kattach, H.; Ratnatunga, C.; Pillai, R.; Channon, K. M.; Casadei, B. A myocardial Nox2 containing NAD(P)H oxidase contributes to oxidative stress in human atrial fibrillation. *Circ Res* 97:629-636; 2005.

Kinnula, V. L. Focus on antioxidant enzymes and antioxidant strategies in smoking related airway diseases. *Thorax* 60:693-700; 2005.

Korantzopoulos, P.; Kolettis, T. M.; Kountouris, E.; Dimitroula, V.; Karanikis, P.; Pappa, E.; Siogas, K.; Goudevenos, J. A. Oral vitamin C administration reduces early recurrence rates after electrical cardioversion of persistent atrial fibrillation and attenuates associated inflammation. *Int J Cardiol* 102:321-326; 2005.

Korantzopoulos, P.; Kolettis, T.M.; Kountouris, E.; Siogas, K.; Goudevenos, J. A. Variation of inflammatory indexes after electrical cardiocersion of persistent atrial fibrillation. Is there an association with early recurrence rates? *Int J Clin Pract* 59:881-885; 2005.

Kumagai, K.; Nakashima, H.; Saku, K. The HMG-CoA reductase inhibitor atorvastatin prevents atrial fibrillation by inhibiting inflammation in a canine sterile pericarditis model. *Cardiovasc Res* 62:105-111; 2004.

Lloyd-Jones, D. M.; Wang, T. J.; Leip, E. P.; Larson, M. G.; Levy, D.; Vasan, R. S.; D'Agostino, R. B.; Massaro, J. M.; Beiser, A.; Wolf, P. A.; Benjamin, E. J. Lifetime risk for development of atrial fibrillation: the Framingham Heart Study. *Circulation* 110:1042-1046; 2004.

Lo, B.; Fijnheer, R.; Nierich, A. P.; Bruins, P.; Kalkman, C. J. C-reactive protein is a risk indicator for atrial fibrillation after myocardial revascularization. *Ann Thorac Surg* 79:1530-1535; 2005.

Malouf, J. F.; Kanagala, R.; Al Atawi, F. O.; Rosales, A. G.; Davison, D. E.; Murali, N. S.; Tsang, T. S.; Chandrasekaran, K.; Ammash, N. M.; Friedman, P. A.; Somers, V. K. High sensitivity C-reactive protein: a novel predictor for recurrence of atrial fibrillation after successful cardioversion. *J Am Coll Cardiol* 46:1284-1287; 2005.

Marin, F.; Pascual, D. A.; Roldan , V.; Arribas, J. M.; Ahumada, M.;Tornel, P. L.; Oliver, C.; Gomez-Plana, J.; Lip, G. Y.; Valdes, M. Statins and postoperative risk of atrial fibrillation following coronary artery bypass grafting. *Am J Cardiol* 97:55-60; 2006.

Mathew, J. P.; Fontes, M. L.; Tudor, I. C.; Ramsey, J.; Duke, P.; Mazer, C. D.; Barash, P. G.; Hsu, P. H.; Mangano, D. T. A multicenter risk index for atrial fibrillation after cardiac surgery. *JAMA* 291:1720-1729; 2004.

Mihm, M. J.; Yu, F.; Carnes, C. A.; Reiser, P. J.; McCarthy, P. M.; Van Wagoner, D. R.; Bauer, J. A. Impaired myofibrillar energetics and oxidative injury during human atrial fibrillation. *Circulation* 104:174-180; 2001.

Moriarty, S. E.; Shah, J. H.; Lynn, M.; Jiang, S.; Openo, K.; Jones, D. P.; Sternberg, P. Oxidation of glutathione and cysteine in human plasma associated with smoking. *Free Radic Biol Med* 35:1582-1588; 2003.

Mozaffarian, D.; Psaty, B. M.; Rimm, E. B.; Lemaitre, R. N.; Burke, G. L.; Lyles, M. F.; Lefkowitz, D.; Siscovick, D. S. Fish intake and risk of incident atrial fibrillation. *Circulation* 110:368-373; 2004.

Ozaydin, M.; Varol, E.; Aslan, S. M.; Kucuktepe, Z.; Dogan, A.; Ozturk, M.; Altinbas, A. Effect of atorvastatin on the recurrence rates of atrial fibrillation after electrical cardioversion. *Am J Cardiol* 97:1490-1493; 2006.

Pike, G. K.; Bretag, A. H.; Roberts, M. L. Modification of the transient outward current of rat atrial myocytes by metabolic inhibition and oxidant stress. *J Physiol* 470:365-382; 1993.

Prasongsukam, K.; Abel, J. G.; Jamieson, W. R.; Cheung, A.; Russell, J. A.; Walley, K. R.; Lichtenstein, S. V. The effects of steroids on the occurrence of postoperative atrial fibrillation after coronary artery bypass grafting surgery: a prospective randomized trial. *J Thorac Cardiovasc Surg* 130:93-98; 2005.

Rahman, I.; MacNee, W. Role of oxidants/antioxidants in smoking-induced lung diseases. *Free Radic Biol Med* 21:669-681; 1996.

Rost, J.; Rapoport, S. Reduction potential of glutathione. *Nature* 201:185; 1964.

Samiec, P. S.; Drews-Botsch, C.; Flagg, E. W.; Kurtz, J. C.; Sternberg, P., Jr.; Reed, R. L.; Jones, D. P. Glutathione in human plasma: decline in association with aging, age-related macular degeneration, and diabetes. *Free Radic Biol Med* 24:699-704; 1998.

Schafer, F. Q.; Buettner, G. R. Redox environment of the cell as viewed through the redox state of the glutathione disulfide/glutathione couple. *Free Radic Biol Med* 30:1191-1212; 2001.

Shang, L. L.; Dudley, S. C., Jr. Tandem promoters and developmentally regulated 5' and 3' mRNA untranslated regions of the mouse scn5a cardiac sodium channel. *J Biol Chem* 280:933-940; 2005.

Shiroshita-Takeshita, A.; Brundel, B. J.; Lavoie, J.; Nattel, S. Prednisone prevents atrial fibrillation promotion by atrial tachycardia remodeling in dogs. *Cardiovasc Res* 69:865-875; 2006.

Shiroshita-Takeshita, A.; Schram, G.; Lavoie, J.; Nattel, S. Effect of simvastatin and antioxidant vitamins on atrial fibrillation promotion by atrial-tachycardia remodeling in dogs. *Circulation* 110:2313-2319; 2004.

Touyz, R. M.; Schiffrin, E. L. Reactive oxygen species in vascular biology: implications in hypertension. *Histochem Cell Biol* 122:339-352; 2004.

Tsubouchi, H.; Inoguchi, T.; Sonta, T.; Sato, N.; Sekiguchi, N.; Kobayashi, K.; Sumimoto, H.; Utsumi, H.; Nawata, H. Statin attenuates high glucose-induced and diabetes-induced and diabetes-induced oxidative stress in vitro and in vivo evaluated by electron spin resonance measurement. *Free Radic Biol Med* 39:444-452; 2005.

Vecchione, C.; Brandes, R. P. Withdrawl of 3-hydroxy-3-methylglutaryl coenzyme A reductase inhibitors elicits oxidative stress and induces endothelial dysfunction in mice. *Circ Res* 91:173-179; 2002.

Wagner, A. H.; Kohler, T.; Ruckschloss, U.; Just, I.; Hecker, M. Improvement of nitric oxide-dependent vasodilatation by HNG-CoA reductase inhibitors through attenuation of endothelial superoxide anion formation. *Arterioscler Thromb Vasc Biol* 20:61-69; 2000.

Wassmann, S.; Laufs, U.; Muller, K.; Konkol, C.; Ahlbory, K.; Baumer, A. T.; Linz, W.; Bohm, M.; Nickenig, G. Cellular antioxidant effects of atorvastatin in vitro and in vivo. *Arterioscler Thromb Vasc Biol* 22:300-305; 2002.

Watanabe, E.; Arakawa, T.; Uchiyama, T.; Kodama, I.; Hishida, H. High-sensitivity C-reactive protein is predictive of successful cardioversion for atrial fibrillation and maintenance of sinus rhythm after conversion. *Int J Cardiol* 108:346-353; 2006.

Yared, J. P.; Starr, N. J.; Torres, F. K.; Bashour, C. A.; Bourdakos, G.; Piedmonte, M.; Michener, J. A.; Davis, J. A.; Rosenberger, T. E. Effects of single dose, postinduction dexamethasone on recovery after cardiac surgery. *Ann Thorac Surg* 69:1420-1424; 2000.

Zarauza, J.; Rodriguez Lera, M. J.; Farinas, A. C.; Hernando, J. P.; Ceballos, B.; Gutierrez, B.; Perez, J.; Cuesta, J. M. Relationship Between C-Reactive Protein Level and Early Recurrence of Atrial Fibrillation After Electrical Cardioversion. *Rev Esp Cardiol* 59:125-129; 2006.

Neuman, R. B.; Bloom. H. L.; Shukrullah, I.; Darrow, L. A.; Kleinbaum, D.; Jones, D. P.; Dudley, Jr. S. C. Oxidative Stress Markers Are Associated with Persistent Atrial Fibrillation. Clinical Chemistry 53:9; published online Jun. 28, 2007, pp. 1-7.

Neuman, R. B.; Bloom, H. L.; Darrow, L. A.; Kleinbaum, D.; Dudley, Jr. S. C. Oxidative stress but not inflammatory markers predict presistent atrial fibrillation. Heart Rhythm Society Meeting, May 20, 2006. Abstract (1 page).

Pietarinen-Runtti, P., Lakari E., Raivio K.O, Kinnula, V.L. Expression of antioxidant enzymes in human inflammatory cells. *Am J Physiol Cell Physiol*. 278:C118-C125, 2000.

* cited by examiner

METHOD FOR PREDICTING ONSET/RISK OF ATRIAL FIBRILLATION (AF)

CROSS-REFERENCE TO RELATED APPLICATIONS

The present application claims priority on prior U.S. Provisional Application Ser. No. 60/835,074, filed Aug. 3, 2006, which is hereby incorporated herein in its entirety by reference.

STATEMENT REGARDING FEDERALLY SPONSORED RESEARCH OR DEVELOPMENT

The work leading to the present invention was supported by one or more grants from the U.S. Government, including NIH Grant(s) HL39006, HL77398, and HL73753, a Department of Veterans Affairs Merit grant (SCD), and a support/grant from the Atlanta Veterans Affairs Medical Center, Health Services Research & Development Program. The U.S. Government therefore has certain rights in the invention.

FIELD AND BACKGROUND OF THE INVENTION

The present invention is generally directed to medical diagnostics, and more particularly to a method for predicting onset/risk of atrial fibrillation in a subject, and guiding an appropriate therapy.

Atrial fibrillation (AF) is by far the most common cardiac arrhythmia. The incidence is high and increasing. The incidence increases twofold with every decade after age 55 years with a prevalence of 5% in people over age 65 (References 5 and 27), and the lifetime risk for AF for people over age 40 is approximately 25%. The number of hospital admissions for AF more than doubled between 1984 and 1994 (Reference 7). Currently, 2.2 million people in the United States have a diagnosis of AF (Reference 36). While generally not lethal, AF reduces the quality of life and increases the risk for systemic embolization, hemodynamic instability, tachycardia-induced cardiomyopathy, and mortality (References 26 and 46). Overall, AF accounts for 15-20% of strokes in the United States, numbering around 75,000 annually (Reference 52).

The pathogenesis of AF is unknown, but studies have supported a role for both oxidative stress and inflammation. Studies of animal and human samples have shown increased myocardial oxidative stress associated with atrial fibrillation (References 9, 24, 47 and 57). Furthermore, anti-oxidants including statins, Vitamin C, polyunsaturated fatty acids, and fish oils reduce the incidence of AF in humans (References 2, 10, 11, 49, 55, 59 and 60).

Inflammation has a complex relationship with oxidative stress and also been associated with AF. There is evidence of inflammatory infiltrates in many cases of lone AF (Reference 29). Elevated levels of the inflammatory marker, C-reactive protein (CRP), are associated with AF in some studies (References 3, 15 and 20) and have been suggested as a predictor of the incidence of AF following cardioversion (References 20, 50, 54 and 75) or cardiac surgery (References 28 and 53). Interleukin-6 (IL-6) is elevated in AF, (Reference 17) and polymorphisms in the IL-6 gene predict the onset of AF after cardiac surgery (Reference 33). Moreover, anti-inflammatory agents seem to reduce the risk of atrial fibrillation (References 21, 22, 40, 56, 62, 68 and 76).

The relative importance of inflammation and oxidative stress in the pathogenesis of AF and which markers might be most strongly associated with the arrhythmia remain unclear. Therefore, we assessed differences in markers of oxidative stress and inflammation between patients with and without persistent of permanent AF.

OBJECTS AND SUMMARY OF THE INVENTION

An object of the present invention is to provide a method for predicting onset/risk of atrial fibrillation (AF) in a subject.

Another object of the present invention is to provide a method for determining the presence of an oxidative stress marker in a subject.

Another object of the present invention is to provide a method for preventing or substantially reducing the risk of atrial fibrillation in a subject.

Another object of the present invention is to provide a method for treating and/or guiding therapy in a subject suspect of having atrial fibrillation.

Another object of the present invention is to provide a method for correcting and/or reversing the side effects of atrial fibrillation in a subject.

Another object of the present invention is to provide a method for reducing the incidence of atrial fibrillation in a population.

Another object of the present invention is to provide a method which would be useful in diagnostic, therapeutic, scientific and other applications regarding atrial fibrillation and related ailments, conditions, or the like.

In summary, AF has been associated with myocardial oxidative stress, and antioxidant agents have demonstrated anti-arrhythmic benefit in humans. In the present invention, serum markers of oxidative stress and inflammation were compared in a cross-sectional, case-control design of 20 male subjects with persistent or permanent AF and controls where cases were matched for age, sex, diabetes, and smoking status, known confounding variables for the measurement of oxidative stress. Derivatives of reactive oxidative metabolites (DROMs) and oxidized to reduced glutathione ($E_h$ GSH) and cysteine ($E_h$ CySH) ratios were used to quantify oxidative stress. Since oxidative stress and inflammation have a complex relationship, inflammatory markers, including high sensitivity C-reactive protein (hsCRP), interleukin-1β (IL-1β), interleukin-6 (IL-6), and tumor necrosis factor-α (TNFα), were also obtained. In univariate, conditional logistical regression analysis, oxidative stress but not inflammatory markers were statistically associated with AF (p<0.05). The increase in the odds for AF for $E_h$ GSH, $E_h$ CySH, and DROMs were, 6.1 (95% CI: 1.3-28.3, p=0.02), 13.6 (95% CI: 2.5-74.1, p=0.01), 15.9 (95% CI: 1.7-153.9, p=0.02), respectively. There was a correlation between $E_h$ GSH and $E_h$ CySH (r=0.66) but not with DROMs (r=0.41). Statins, known antioxidants, were negatively associated with the presence of AF (OR=0.2; 95% CI 0.05-0.99; p=0.05). In multivariate analysis, correcting for statins and other AF risk factors, the association between AF and oxidative stress remained significant. These data suggest an association between oxidative stress and AF. Oxidative stress markers appeared to have a stronger association with AF than did inflammatory markers.

At least one of the above objects is met, in part, by the present invention, which in one aspect includes a method for predicting onset or risk of atrial fibrillation in a subject, including determining the presence of an oxidative stress marker.

Another aspect of the present invention includes a method for treating a subject suspect of having atrial fibrillation, including a) determining the presence of an elevated blood level of an oxidative stress marker, b) comparing the value obtained in step a) to a predetermined normal value, and c) recommending the subject for an antioxidant therapy if the value obtained in step b) is higher than the normal value.

BRIEF DESCRIPTION OF THE DRAWINGS

At least one of the above objects, novel features and advantages of the present invention will become apparent from the following detailed description of the invention, as illustrated in the drawings, in which:

FIG. 1 illustrates difference in the oxidative stress markers between subjects with and without atrial fibrillation.

DETAILED DESCRIPTION OF THE INVENTION

Materials and Methods

Study Population

Figure 1A:
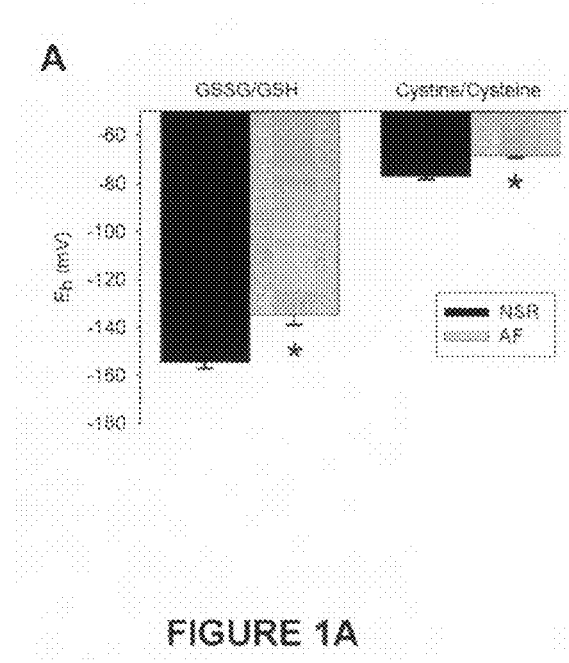
FIG. 1A: Both the oxidized (GSSG) to reduced (GSH) glutathione and oxidized (cysteine) to reduced cysteine thiol couples indicated a more oxidized state (i.e., a less negative $E_h$) in subjects with AF (grey bars) as compared to matched controls in normal sinus rhythm (NSR, black bars).

This cross-sectional, case-control study recruited patients in AF from outpatient clinics at the Atlanta Veterans Affairs Medical Center (VAMC) from May through July of 2005 under a protocol approved by the Emory University Institutional Review Board (www.clinicaltrials.gov: NCT00142194). Eligible patients were over 18 years of age and in persistent or permanent AF at the time of enrollment. Ineligibility criteria included systemic inflammatory diseases, malignant neoplasm, severe stenotic or regurgitant valvular heart disease, New York Heart Association class IV heart failure, hyperthyroidism, uncontrolled hypertension (>180/100 at rest), an illness that may have resulted in death within one year, implanted devices designed for the active management of atrial arrhythmias by pacing or defibrillation, and current illicit drug or alcohol abuse.

Control patients were identified from outpatient clinic visits at the Atlanta VAMC over the same period of time. The same eligibility and ineligibility criteria applied with the exception that control patients were free of current AF and any history of AF as documented by an electrocardiogram (ECG) performed at the time of enrollment, history, and review of the medical record. Cases and control subjects were matched for factors known to affect the oxidative markers used, age in decades, smoking, and diabetes status (References 25, 44, 48, 58, 63 and 65). All patients enrolled gave written consent.

Data Collected

Data was collected from subject interviews, review of VA hospital and clinic charts, telemetry recordings, and ECGs. The presence or absence of AF was confirmed on the basis of an ECG done at the time of enrollment. Demographic data obtained included: age, race, body mass index, New York Heart Association (NYHA) functional class, and a history of previous myocardial infarction, hypertension, diabetes, smoking, or alcohol use. Additionally, all medications being taken at the time of enrollment were recorded. A single blood draw was performed at the time of enrollment and analyzed for markers of oxidative stress and inflammation in the Emory Biomarkers Core Laboratory.

Markers used to measure oxidative stress were: ratios of oxidized to reduced glutathione ($E_h$ GSH) and cysteine ($E_h$ CySH) in plasma (thiol ratios) (References 41-44) and derivatives of reactive oxygen species (DROMs) (also known as the Free Oxygen Radicals Test—FORT) (References 1, 12, 18 and 38). Detailed methods to prevent rapid oxidation of samples have been delineated previously (Reference 43). Briefly, blood was collected from an antecubital vein transferred immediately to a microcentrifuge tube containing 0.5 mL of a preservation solution of 100 mM serine-borate (pH 8.5) containing (per mL) 0.5 mg sodium heparin, 1 mg bathophenanthroline disulfonate sodium salt, and 2 mg iodoacetic acid. Use of this procedure minimizes autoxidation and hemolysis (Reference 43). Following centrifugation to remove blood cells, aliquots (200 μL) were transferred to tubes containing 200 μL of 10% (w/v) perchloric acid containing 0.2 M boric acid and 10 μM γ-Glu-Glu as internal standard. Samples were stored at −80° C. (<2 months) prior to further processing to form N-dansyl derivatives and analysis by HPLC with fluorescence detection. Previous data have shown stable measurements with this length of storage (Reference 43). Metabolites were identified by co-elution with standards, and quantification was obtained by integration relative to the internal standard. Samples from control and AF patients were treated identically.

The redox states ($E_h$) of the thiol/disulfide pools were calculated with the Nernst equation, $E_h = E_o + RT/nF \ln[\text{disulfide}]/[\text{thiol}]^2$, where $E_o$ is the standard potential for the redox couple, R is the gas constant, T is the absolute temperature, n is 2 for the number of electrons transferred, and F is Faraday's constant (References 64 and 66). The standard potential $E_o$ used for the glutathione and cysteine redox couples was −264 mV and −250 mV, respectively (Reference 43). Less negative $E_h$ numbers imply a more oxidized state. DROMs were measured in Carr units with higher values indicating higher levels of oxidative stress. DROMs (Diacron International, Grosseto, Italy) and inflammatory markers, high sensitivity C-reactive protein (hsCRP; Life Diagnostics, West Chester, Pa.), interleukin-1-β (IL-1β; R&D Systems, Minneapolis, Minn.), interleukin-6 (IL-6; R&D Systems), and tumor necrosis factorα (TNFα; R&D Systems), were measured using commercially available kits. Intraassay CVs were <1% at −156 and <1% at −120 mV for $E_h$ GSH, 5.0% at −100 and 4.5% at −60 mV for $E_h$ CySH, 0.2% at 300 and 2.3% at 550 Carr units for DROMs; 10.1% at 0.2 and 5.2% at 10 ng/L for IL-1β, 5.1% at 1 and 3.6% at 8 mg/L for hsCRP, 20.9% at 3.2 and 6.2% at 50 ng/L for IL-6, and, 11.9% at 2 and 7.3 at 50 ng/L for TNFα.

Data Analysis

Statistical analysis was performed using SAS software 9.1 (SAS Institute, Cary, N.C., USA). Baseline characteristics of AF patients and their matched controls were compared using a paired t-test for continuous variables (expressed as mean ±SD), and Fisher's exact test for categorical variables.

All statistical tests were two-tailed, and significance was assumed at p≦0.05. Correlations between markers of inflammation and oxidative stress were assessed using Spearman rank-order correlation coefficients. All oxidative and inflammatory markers were examined as predictors of AF occurrence in single-variate conditional logistic regression models; age category, smoking and diabetes status were accounted for by matching. Variables exhibiting borderline normality were also examined after logarithmic transformation. Parameter estimates for each oxidative and inflammatory marker were scaled so that reported odds ratios correspond to an approximate inter-quartile range increase. Using the parameter estimate from the $E_h$ GSH model, odds ratios for AF were computed and plotted as a function of increase in $E_h$ GSH level. Multivariate conditional logistic regression models were used to examine the association between each oxidative marker and the presence of AF while controlling for inflammatory markers. Statins were assessed as predictors of AF presence and in linear regression models as predictors of $E_h$ GSH.

Results

Twenty subjects with persistent or permanent AF along with 20 individuals free of AF were compared in the study. Control subjects were matched to cases by age, sex, smoking and diabetes status because these variables are known to affect the oxidative stress measures used (References 25, 44, 48, 58, 63 and 65) Table 1 (below) compares the demographics of cases and their controls. The AF subjects had ages ranging from 58-86 with a mean age of 74.8 years. Five subjects (25%) were diabetic. All AF subjects were male and non-smokers. The mean length of AF was 10.1 years with a median of 6.4±13.3 years. In non-matched variables, hypertension and heart failure were slightly more common in the AF group, consistent with these conditions predisposing to the arrhythmia (References 5, 16, 31 and 45). In all other parameters, the populations were statistically similar (p>0.05).

Figure 1B:
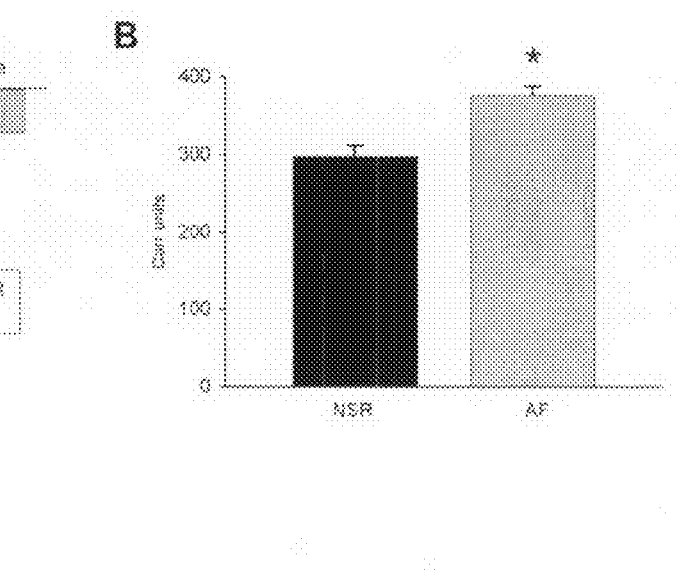
FIG. 1B: DROMs were evaluated in the AF group (grey bars) as compared to the controls in normal sinus rhythm (NSR, black bars). * indicates a $p<0.05$.

All measures of oxidative stress were significantly increased in AF patients compared with controls. Thiol ratios in the AF group were significantly more oxidized (i.e., negative) than in the controls (p<0.001; FIG. 1A). The AF group showed more oxidation, with a mean (SD) $E_h$ GSH of −133 (21) mV (median −143 mV, interassay CV, 15.8%) and $E_h$ CySH of −68 (6) mV (median −67 mV, CV=8.8%) compared to the control group, which had a mean (SD) $E_h$ GSH of −154 (12) mV (median −156 mV, CV 7.8%) and $E_h$ CySH of −77 (6) mV (median −76, CV 7.8%). Consistent with the thiol results, the DROMs also showed more oxidation in the AF group [388 (54) Carr units, median 370 Carr units, CV 13.9%] than the controls [310 (44) Carr units, median 308 Carr units, CV 14.2%] (p=0.001; FIG. 1B).

The inflammatory markers IL-1β, IL-6, TNFα, and hsCRP were mildly, but insignificantly increased in the AF group compared to controls. Mean (SD) values for IL-1β, IL-6, TNFα, and hsCRP in the AF group were 0.5 (0.8) ng/L (median 0.3), 5.5 (3.9) ng/L (median 4.2), 6.5 (8.1) ng/L (median 3.8), and 5.1 (3.8) mg/L (median 4.5) compared to 0.4 (0.4) ng/L (median 0.3), 3.9 (1.6) ng/L (median 3.6), 5.5 (3.4) ng/L (median 4.7), and 3.6 (3.1) μg/mL (median 2.6) for the control group, respectively.

Figure 2:
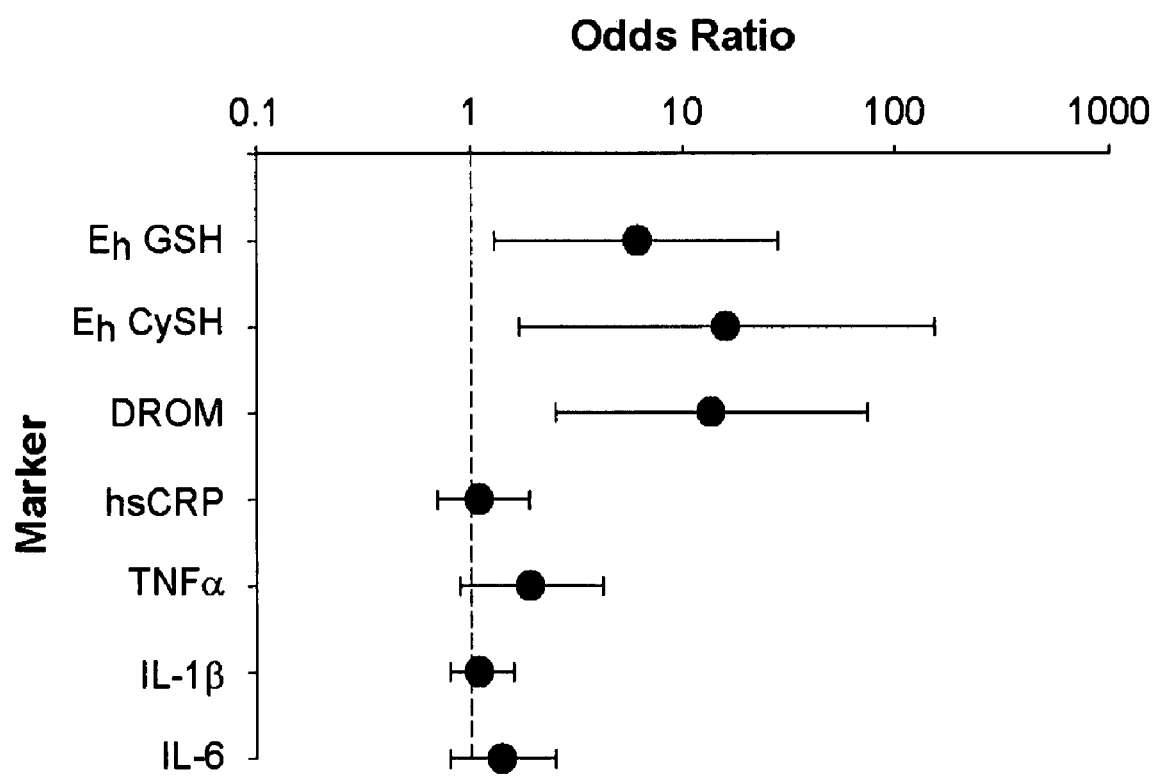
FIG. 2 illustrates the univariate odd ratios for atrial fibrillation as a function of an interquartile increase in various markers. Only the oxidative stress markers ($E_h$ GSH, $E_h$ CySH, and DROMs) showed a significant association with AF.

The relationship of oxidative stress and inflammatory markers to AF was analyzed in single exposure conditional logistical models. The odds ratios for AF were computed based on an inter-quartile range increase for each single marker; comparing the risk of AF in subjects at the 25$^{th}$ percentile to those at the 75$^{th}$ percentile. Single exposure model odds ratios were controlled for matching variables of age, sex, smoking, and diabetes status, but are otherwise unadjusted. Oxidative stress markers, $E_h$ GSH, $E_h$ CySH, and DROMs, all predict AF with odds ratios of 6.1 (95% CI: 1.3-28.3, p=0.02), 13.6 (95% CI: 2.5-74.1, p=0.01), 15.9 (95% CI: 1.7-153.9, p=0.02) respectively (Table 2 below). None of the odds ratios for any of the four inflammatory markers measured were statistically significant (FIG. 2, p>0.05).

There is a complex relationship between oxidative stress and inflammation. To evaluate this further, we compared the correlations between markers in our study (Table 3 below). Consistent with the idea that thiol ratios best represent the redox states of the hydrophilic phase while DROMs more likely measure the redox state of a lipid phase, Spearman correlation coefficients revealed a statistically significant correlation between $E_h$ GSH and $E_h$ CySH (r=0.66) while the relationship of thiol ratios to DROMs was weaker (Table 3). For the most part, oxidative stress markers were independent of inflammatory markers, except for the case of a statistically significant positive correlation between TNFα and DROMs (r=0.38) and a negative correlation between TNFα and $E_h$ CySH (r=−0.42). On the other hand, most inflammatory markers showed a significant degree of correlation between each other.

Because statins are postulated to have antioxidant activity and have been associated with a reduced incidence of AF (References 2, 55 and 60), we analyzed the relationship between use of statins and AF among patients in our study. Statin use was negatively correlated with AF with an OR of 0.2 (95% CI 0.05-0.99, p=0.05). Moreover, linear regression analysis revealed that $E_h$ GSH and statins were associated with a 14.3 mV (95% CI 0.8-27.8) decrease in the oxidative stress marker, $E_h$ GSH, suggesting that the statin effect of AF may be related to a reduction in oxidative stress. In multivariate analyses, the association of AF and more oxidized thiol ratios remained statistically significant when correcting for hypertension, congestive heart failure, and statin use.

Discussion

Oxidative stress has been implicated in the pathogenesis of AF. The purpose of this study was to compare the relative changes in oxidative stress markers between patients with and without persistent or permanent AF. We found that oxidative stress markers differed between the two groups. Inter-quartile range increases across all markers of oxidative stress strongly and significantly correlated with increased risk of AF. This remained true even after correction for differences in hypertension, congestive heart failure, and statin use between the two groups.

Oxidative Stress and AF

Figure 3:
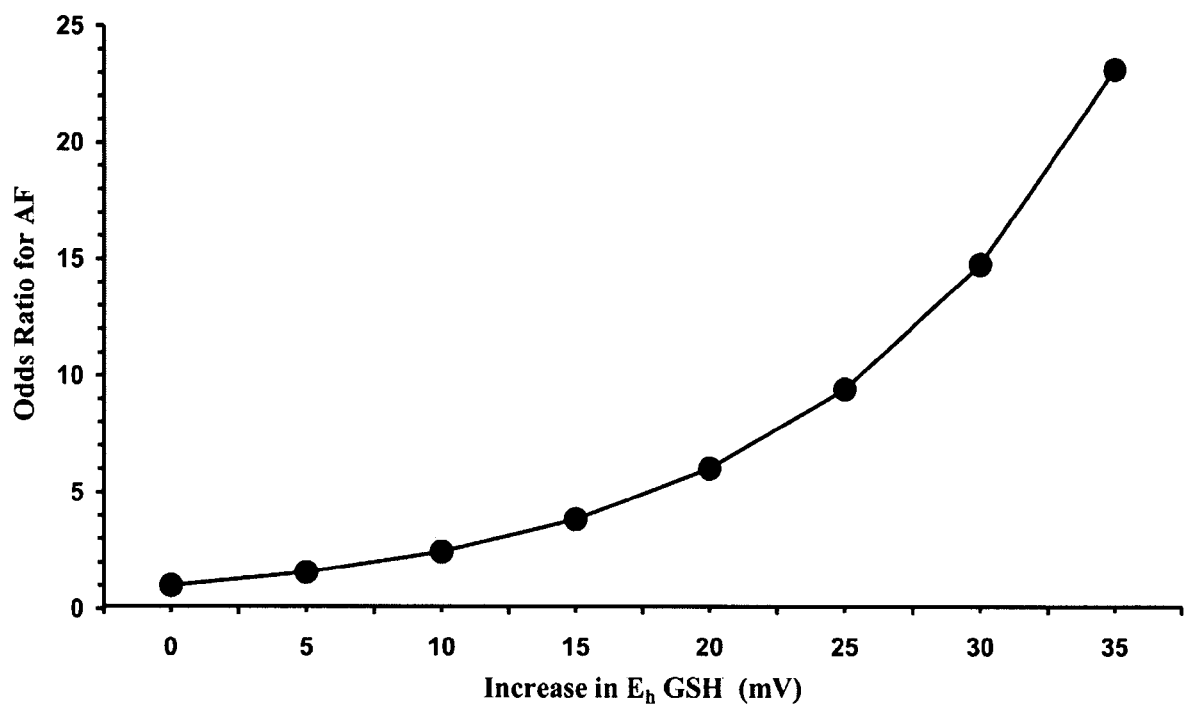
FIG. 3 illustrates the odds ratio for atrial fibrillation for a given change in $E_h$ GSH. The logistical regression model predicts that as the glutathione thiol couple becomes more oxidized, there is a progressive increase in the odds ratio for AF.

The strong correlation of AF with oxidative stress markers may suggest novel measures to predict the onset and efficacy of treatment in AF. FIG. 3 shows the relationship of $E_h$ GSH to the odds ratio for AF based on the parameters determined in the multivariate logistical regression analysis. A change in $E_h$ GSH of 15 mV implies a ~4 fold increase in the odds ratio of AF. This change in $E_h$ GSH corresponds to roughly that expected with either a decade increase in age or the presence of diabetes, hypertension, or smoking, all known risk factors for AF (References 44, 58 and 65). The mechanisms whereby oxidative stress may contribute to AF are unknown, but there is evidence that oxidants can affect ion channel activity (References 4, 30 and 61). Also, oxidative stress is known to activate redox sensitive transcription factors such as NF-κB. Recently, we have shown that the cardiac sodium channel (SCN5a) promoter region contains an NF-κB response element that could lead to Na+ channel transcriptional regulation by a NFκB-dependent mechanism (Reference 67).

Statins and AF

In our study, we showed an inverse relationship between statin use and oxidative stress or the incidence of AF. Statins are thought to have anti-oxidant properties at least in part as a result of preventing NADPH oxidase induced oxygen free radical production (References 14 and 71-74). Our findings are consistent with reports that statins prevent electrical remodeling in rapid pacing-induced AF (Reference 69) and experimentally induced sterile pericarditis (Reference 51) in canine models and reducing AF burden after cardiac (Reference 55) or non-cardiac surgeries (Reference 2). Moreover, it is consistent with a recent report of statins preventing recurrence of AF after cardioversion (Reference 60).

Inflammation and AF

Since inflammation has been associated with AF and oxidative stress, we also measured inflammatory markers between our two groups. We did not find an association in our study, however. This is consistent with findings of several other groups investigating the use of CRP to predict post-operative AF (References 2, 33, 34 and 77). Conway et al. found that CRP predicted only initial but not long term cardioversion success, (Reference 17). Conversely, other reports suggest a correlation of inflammatory markers with AF. There is a well documented increase in AF incidence after cardiac surgery, this increase in AF correlates temporally with the peak elevation in CRP levels (Reference 8). Moreover, in two trials, patients with high CRP levels were more likely to develop AF (References 3 and 53). A recent meta-analysis of 16 trials does suggest a relationship between inflammation and persistent or permanent AF (Reference 6). In one trial, IL-6 but not CRP or TNFα predicted post-operative AF (Reference 39). The concomitant lack of elevation of IL-1β, IL-6, and CRP is consistent with the known roles of these interleukins as synergistic upstream stimuli for CRP production (Reference 32).

Since our patients had persistent or permanent AF, the association of AF with oxidative stress but not inflammatory markers could represent a more prominent role for oxidative stress relative to inflammation in the maintenance of AF. Alternatively, differences in post-operative and non-operative AF, a lack of sensitivity given our high baseline CRP levels compared to other trials, or the limited power of the trial to detect a relationship could explain the findings. Our levels of IL-6 and TNFα were comparable with baseline levels in a recent report, however, suggesting that our patients were not substantially different in inflammatory state from those in other trials (Reference 39). Although our results do not directly address the role of oxidative stress in the initiation of AF, they do not rule out a potential role for inflammation in the maintenance of AF. Interestingly, cardiac surgery has also been reported to increase oxidative stress as measured by thiol ratios in the plasma and myocardium, (Reference 19) and supplementing postoperative patients with ascorbate, a known anti-oxidant, cuts rates of AF over 2-fold (Reference 11).

Figure 4:
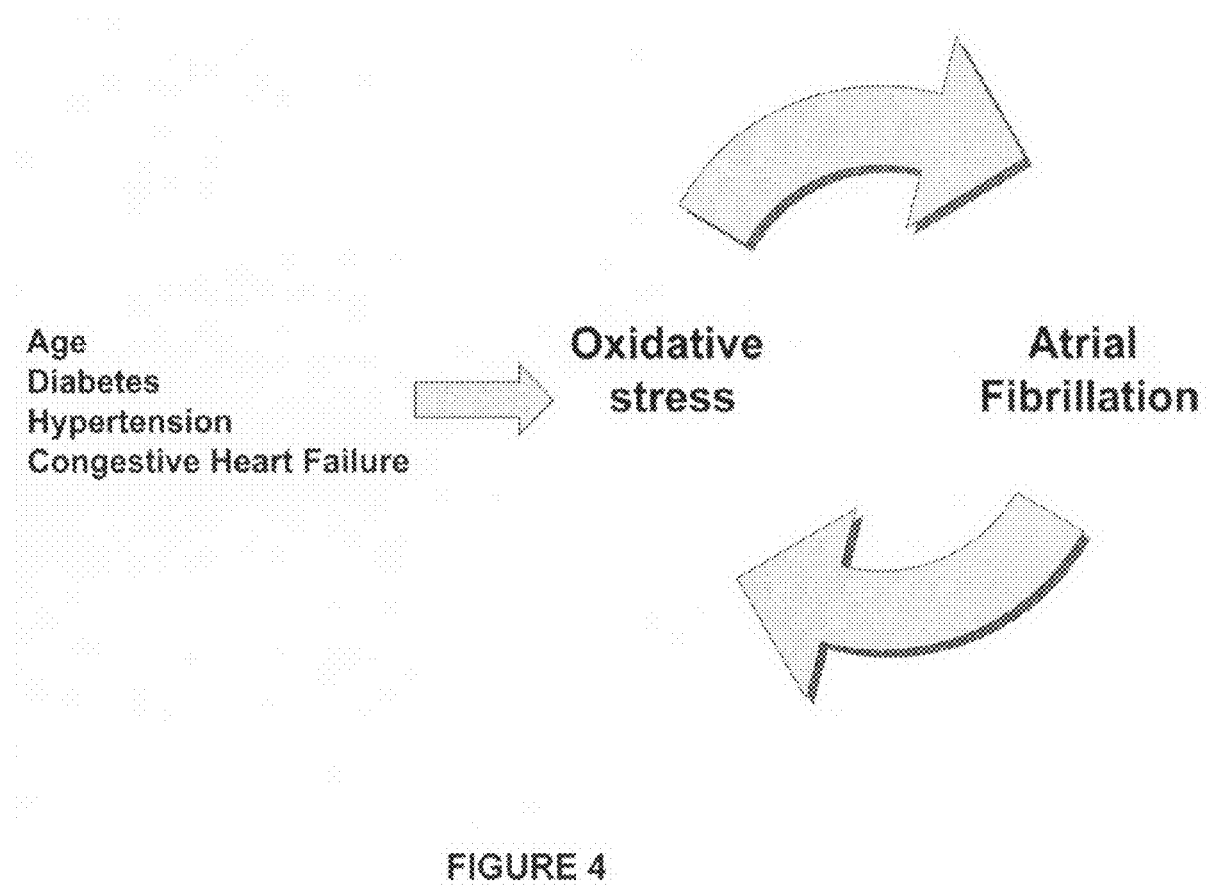
FIG. 4 illustrates a unified hypothesis explaining the relationship of AF and its risk factors to oxidative stress. This hypothesis is consistent with the association of AF and certain AF risk factors with oxidative stress.

As noted above, AF has been associated with cardiac oxidative stress, but a recent trial suggests that oxidative stress in AF may be more widespread (Reference 35). Therefore, it is possible that systemic oxidative stress contributes to AF risk and, once AF is established, local cardiac oxidative stress reinforces the risk (References 23 and 47). Interestingly, congestive heart failure and hypertension are associated with oxidative stress, perhaps contributing to their unequal distribution between the two groups (References 13, 37 and 70). A hypothesis potentially explaining the relationship of AF and its risk factors to oxidative stress is presented in FIG. 4.

In conclusion, persistent or permanent AF is associated with increased blood markers of oxidative stress when compared to an age-, sex-, smoking-, and diabetes-matched control population. In this study, the use of statins was associated with a lower prevalence of AF and with decreased oxidative stress levels. Therefore, lower oxidative stress marker levels may predict a lower risk of AF or efficacy of drugs in the prevention of AF.

TABLE 1

Comparison of Baseline characteristics

| Variable | Cases (N = 20) | Controls (N = 20) | p-value* |
|---|---|---|---|
| Age[†] | 74.8 ± 8.8 | 74.5 ± 8.5 | 0.74 |
| Diabetic[†] | 25% (5) | 25% (5) | 1.00 |
| BMI | 27.7 ± 4.8 | 28.3 ± 5.2 | 0.71 |
| Race | | | |
| white | 18 (90%) | 18 (90%) | 1.00 |
| black | 2 (10%) | 2 (10%) | |
| Prior MI[‡] | 4 (20%) | 6 (30%) | 0.72 |
| Hypertensive | 16 (80%) | 9 (45%) | 0.05 |
| NYHA Class | | | |
| class 1 | 8 (40%) | 16 (80%) | 0.04 |
| class 2 | 9 (45%) | 3 (15%) | |
| class 3 | 3 (15%) | 1 (5%) | |
| Number of medications | 8.2 ± 3.4 | 6.4 ± 4.1 | 0.13 |
| Use of Statins | 5 (25%) | 11 (55%) | 0.11 |

*t-test or Fisher's Exact two-sided p-values for continuous or categorical variables, respectively
[†]Matching variable
[‡]MI indicates myocardial infarction

TABLE 2

Univariate Increase in the Odds of Atrial Fibrillation for an Inter-Quartile Range Increase in Oxidative and Inflammatory Markers

| Exposure Variable | Unit increase* | Odds Ratio | 95% Confidence Interval | p-value |
|---|---|---|---|---|
| Oxidative markers | | | | |
| $E_h$ GSH | 20 | 6.1 | 1.3, 28.3 | 0.02 |
| $E_h$ CySH | 10 | 13.6 | 2.5, 74.1 | 0.01 |
| DROMs | 70 | 15.9 | 1.7, 153.9 | 0.02 |
| Inflammatory markers | | | | |
| IL-1β | 0.35 | 1.1 | 0.8, 1.6 | 0.59 |
| IL-6 | 3 | 1.9 | 0.9, 4.2 | 0.11 |
| TNFα | 5 | 1.1 | 0.7, 1.9 | 0.61 |
| hsCRP | 3 | 1.4 | 0.8, 2.5 | 0.21 |

*Approximate increase in the number of measured units (e.g. mV for thiol ratios, Carr units for DROMs, pg/mL for IL-1β, IL-6, and TNFα, and μg/mL for hsCRP, respectively) needed to move from the 25th to 75th percentile.

TABLE 3

Spearman Correlation Coefficients Between Markers

| Marker | $E_h$ GSH | $E_h$ CySH | DROMs | hsCRP | TNFα | IL-1β | IL-6 |
|---|---|---|---|---|---|---|---|
| $E_h$ GSH | 1 | 0.66* | 0.41 | 0.29 | −0.16 | 0.00 | 0.05 |
| $E_h$ CySH | | 1 | 0.38* | −0.02 | −0.42* | −0.21 | −0.16 |
| DROMs | | | 1 | 0.29 | 0.02 | −0.01 | 0.38* |
| hsCRP | | | | 1 | 0.19 | 0.14 | 0.40* |

TABLE 3-continued

Spearman Correlation Coefficients Between Markers

| Marker | $E_h$ GSH | $E_h$ CySH | DROMs | hsCRP | TNFα | IL-1β | IL-6 |
|---|---|---|---|---|---|---|---|
| TNFα | | | | | 1 | 0.57* | 0.47* |
| IL-1β | | | | | | 1 | 0.42* |
| IL-6 | | | | | | | 1 |

*p < 0.05

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, and those cited in the disclosure herein, are hereby incorporated herein in their entirety by reference.

1. Abramson, J. L.; Hooper, W. C.; Jones, D. P.; Ashfaq, S.; Rhodes, S. D.; Weintraub, W. S.; Harrison, D. G.; Quyyumi, A. A.; Vaccarino, V. Association between novel oxidative stress markers and C-reactive protein among adults without clinical coronary heart disease. *Atherosclerosis* 178:115-121; 2005.
2. Amar, D.; Zhang, H.; Heerdt, P. M.; Park, B.; Fleisher, M.; Thaler, H. T. Statin use is associated with a reduction in atrial fibrillation after noncardiac thoracic surgery independent of C-reactive protein. *Chest* 128:3421-3427; 2005.
3. Aviles, R. J.; Martin, D. O.; Apperson-Hansen, C.; Houghtaling, P. L.; Rautaharju, P.; Kronmal, R. A.; Tracy, R. P.; Van Wagoner, D. R.; Psaty, B. M.; Lauer, M. S.; Chung, M. K. Inflammation as a risk factor for atrial fibrillation. *Circulation* 108:3006-3010; 2003.
4. Barrington, P. L.; Martin, R. L.; Zhang, K. Slowly inactivating sodium currents are reduced by exposure to oxidative stress. *J Mol Cell Cardiol* 29:3251-3265; 1997.
5. Benjamin, E. J.; Levy, D.; Vaziri, S. M.; D'Agostino, R. B.; Belanger, A. J.; Wolf, P. A. Independent risk factors for atrial fibrillation in a population-based cohort. The Framingham Heart Study. *JAMA* 271:840-844; 1994.
6. Boos, C. J.; Anderson, R. A.; Lip, G. Y. Is atrial fibrillation an inflammatory disorder? *Eur Heart J* 27:136-149; 2006.
7. Braunwald, E. Shattuck lecture—cardiovascular medicine at the turn of the millennium: triumphs, concerns, and opportunities. *N Engl J Med* 337:1360-1369; 1997.
8. Bruins, P.; te, V. H.; Yazdanbakhsh, A. P.; Jansen, P. G.; van Hardevelt, F. W.; de Beaumont, E. M.; Wildevuur, C. R.; Eijsman, L.; Trouwborst, A.; Hack, C. E. Activation of the complement system during and after cardiopulmonary bypass surgery: postsurgery activation involves C-reactive protein and is associated with postoperative arrhythmia. *Circulation* 96:3542-3548; 1997.
9. Cai, H.; Li, Z.; Goette, A.; Mera, F.; Honeycutt, C.; Feterik, K.; Wilcox, J. N.; Dudley, S. C., Jr.; Harrison, D. G.; Langberg, J. J. Downregulation of endocardial nitric oxide synthase expression and nitric oxide production in atrial fibrillation: potential mechanisms for atrial thrombosis and stroke. *Circulation* 106:2854-2858; 2002.
10. Calo, L.; Bianconi, L.; Colivicchi, F.; Lamberti, F.; Loricchio, M. L.; de Ruvo, E.; Meo, A.; Pandozi, C.; Staibano, M.; Santini, M. N-3 Fatty acids for the prevention of atrial fibrillation after coronary artery bypass surgery: a randomized, controlled trial. *J Am Coll Cardiol* 45:1723-1728; 2005.
11. Carnes, C. A.; Chung, M. K.; Nakayama, T.; Nakayama, H.; Baliga, R. S.; Piao, S.; Kanderian, A.; Pavia, S.; Hamlin, R. L.; McCarthy, P. M.; Bauer, J. A.; Van Wagoner, D. R. Ascorbate attenuates atrial pacing-induced peroxynitrite formation and electrical remodeling and decreases the incidence of postoperative atrial fibrillation. *Circ Res* 89:E32-E38; 2001.
12. Cesarone, M. R.; Belcaro, G.; Carratelli, M.; Cornelli, U.; De Sanctis, M. T.; Incandela, L.; Barsotti, A.; Terranova, R.; Nicolaides, A. A simple test to monitor oxidative stress. *Int Angiol* 18:127-130; 1999.
13. Choudhary, G.; Dudley, S. C., Jr. Heart failure, oxidative stress, and ion channel modulation. *Congest Heart Fail* 8:148-155; 2002.
14. Christ, M.; Bauersachs, J.; Liebetrau, C.; Heck, M.; Gunther, A.; Wehling, M. Glucose increases endothelial-dependent superoxide formation in coronary arteries by NAD(P)H oxidase activation: attenuation by the 3-hydroxy-3-methylglutaryl coenzyme A reductase inhibitor atorvastatin. *Diabetes* 51:2648-2652; 2002.
15. Chung, M. K.; Martin, D. O.; Sprecher, D.; Wazni, O.; Kanderian, A.; Carnes, C. A.; Bauer, J. A.; Tchou, P. J.; Niebauer, M. J.; Natale, A.; Van Wagoner, D. R. C-reactive protein elevation in patients with atrial arrhythmias: inflammatory mechanisms and persistence of atrial fibrillation. *Circulation* 104:2886-2891; 2001.
16. Ciaroni, S.; Cuenoud, L.; Bloch, A. Clinical study to investigate the predictive parameters for the onset of atrial fibrillation in patients with essential hypertension. *Am Heart J* 139:814-819; 2000.
17. Conway, D. S.; Buggins, P.; Hughes, E.; Lip, G. Y. Relationship of interleukin-6 and C-reactive protein to the prothrombotic state in chronic atrial fibrillation. *J Am Coll Cardiol* 43:2075-2082; 2004.
18. Cornelli, U.; Terranova, R.; Luca, S.; Cornelli, M.; Alberti, A. Bioavailability and antioxidant activity of some food supplements in men and women using the D-Roms test as a marker of oxidative stress. *J Nutr* 131:3208-3211; 2001.
19. De Vecchi, E.; Pala, M. G.; Di Credico, G.; Agape, V.; Paolini, G.; Bonini, P. A.; Grossi, A.; Paroni, R. Relation between left ventricular function and oxidative stress in patients undergoing bypass surgery. *Heart* 79:242-247; 1998.
20. Dernellis, J.; Panaretou, M. C-reactive protein and paroxysmal atrial fibrillation: evidence of the implication of an inflammatory process in paroxysmal atrial fibrillation. *Acta Cardiol* 56:375-380; 2001.
21. Dernellis, J.; Panaretou, M. Relationship between C-reactive protein concentrations during glucocorticoid therapy and recurrent atrial fibrillation. *Eur Heart J* 25:1100-1107; 2004.
22. Dernellis, J.; Panaretou, M. Effect of C-reactive protein reduction on paroxysmal atrial fibrillation. *Am Heart J* 150:1064; 2005.
23. Dudley, S. C., Jr.; Diamandopoulus, L.; Dikalov, S.; Fink, B.; Fink, N.; McCann, L.; Honeycutt, C.; Mera, F.; Harrison, D. G.; Langberg, J. J. Atrial fibrillation causes increased oxidative stress and decreased nitric oxide bioavailability in the left atrial appendage. *Circulation* 108: IV-147-IV-148. (2003)

24. Dudley, S. C., Jr.; Hoch, N. E.; McCann, L. A.; Honeycutt, C.; Diamandopoulus, L.; Fukai, T.; Harrison, D. G.; Langberg, J. Atrial fibrillation increases production of superoxide by the left atrium and left atrial appendage: role of the NADPH and xanthine oxidases. *Circulation* 112:1266-1273; 2005.

25. Durak, I.; Elgun, S.; Kemal, B. N.; Burak Cimen, M. Y.; Kacmaz, M.; Buyukkocak, S.; Serdar, O. H. Effects of cigarette smoking with different tar content on erythrocyte oxidant/antioxidant status. *Addiction Biology* 7:255-258; 2002.

26. Falk, R. H. Impact of prospective peer review on pacemaker implantation rates in Massachusetts. *J Am Coll Cardiol* 15:1087-1092; 1990.

27. Feinberg, W. M.; Blackshear, J. L.; Laupacis, A.; Kronmal, R.; Hart, R. G. Prevalence, age distribution, and gender of patients with atrial fibrillation. Analysis and implications. *Arch Intern Med* 155:469-473; 1995.

28. Fontes, M. L.; Mathew, J. P.; Rinder, H. M.; Zelterman, D.; Smith, B. R.; Rinder, C. S. Atrial fibrillation after cardiac surgery/cardiopulmonary bypass is associated with monocyte activation. *Anesth Analg* 101:17-23, table; 2005.

29. Frustaci, A.; Chimenti, C.; Bellocci, F.; Morgante, E.; Russo, M. A.; Maseri, A. Histological substrate of atrial biopsies in patients with lone atrial fibrillation. *Circulation* 96:1180-1184; 1997.

30. Fukuda, K.; Davies, S. S.; Nakajima, T.; Ong, B. H.; Kupershmidt, S.; Fessel, J.; Amarnath, V.; Anderson, M. E.; Boyden, P. A.; Viswanathan, P. C.; Roberts, L. J.; Balser, J. R. Oxidative mediated lipid peroxidation recapitulates proarrhythmic effects on cardiac sodium channels. *Circ Res* 97:1262-1269; 2005.

31. Furberg, C. D.; Psaty, B. M.; Manolio, T. A.; Gardin, J. M.; Smith, V. E.; Rautaharju, P. M. Prevalence of atrial fibrillation in elderly subjects (the Cardiovascular Health Study). *Am J Cardiol* 74:236-241; 1994.

32. Ganter, U.; Arcone, R.; Toniatti, C.; Morrone, G.; Ciliberto, G. Dual control of C-reactive protein gene expression by interleukin-1 and interleukin-6. *EMBO J.* 8:3773-3779; 1989.

33. Gaudino, M.; Andreotti, F.; Zamparelli, R.; Di Castelnuovo, A.; Nasso, G.; Burzotta, F.; Iacoviello, L.; Donati, M. B.; Schiavello, R.; Maseri, A.; Possati, G. The −174G/C interleukin-6 polymorphism influences postoperative interleukin-6 levels and postoperative atrial fibrillation. Is atrial fibrillation an inflammatory complication? *Circulation* 108 Suppl 1:II195-II199; 2003.

34. Goette, A.; Juenemann, G.; Peters, B.; Klein, H. U.; Roessner, A.; Huth, C.; Rocken, C. Determinants and consequences of atrial fibrosis in patients undergoing open heart surgery. *Cardiovasc Res* 54:390-396; 2002.

35. Guazzi, M.; Belletti, S.; Bianco, E.; Lenatti, L.; Maurizio, G. D. Endothelial dysfunction and exercise performance in lone atrial fibrillation or associated with hypertension or diabetes. Different results with cardioversion. *Am J Physiol* 2006.

36. Hart, R. G.; Halperin, J. L. Atrial fibrillation and stroke: concepts and controversies. *Stroke* 32:803-808; 2001.

37. Heymes, C.; Bendall, J. K.; Ratajczak, P.; Cave, A. C.; Samuel, J. L.; Hasenfuss, G.; Shah, A. M. Increased myocardial NADPH oxidase activity in human heart failure. *J Am Coll Cardiol* 41:2164-2171; 2003.

38. Incandela, L.; Belcaro, G.; Cesarone, M. R.; De Sanctis, M. T.; Griffin, M.; Cacchio, M.; Nicolaides, A. N.; Bucci, M.; Barsotti, A.; Martines, G.; Cornelli, U.; Di Renzo, A. Oxygen-free radical decrease in hypertensive patients treated with lercanidipine. *Int Angiol* 20:136-140; 2001.

39. Ishida, K.; Kimura, F.; Imamaki, M.; Ishida, A.; Shimura, H.; Kohno, H.; Sakurai, M.; Miyazaki, M. Relation of inflammatory cytokines to atrial fibrillation after off-pump coronary artery bypass grafting. *Eur J Cardiothoracic Surg* 29:501-505; 2006.

40. Ishii, Y.; Schuessler, R. B.; Gaynor, S. L.; Yamada, K.; Fu, A. S.; Boineau, J. P.; Damiano, R. J., Jr. Inflammation of atrium after cardiac surgery is associated with inhomogeneity of atrial conduction and atrial fibrillation. *Circulation* 111:2881-2888; 2005.

41. Jonas, C. R.; Puckett, A. B.; Jones, D. P.; Griffith, D. P.; Szeszycki, E. E.; Bergman, G. F.; Furr, C. E.; Tyre, C.; Carlson, J. L.; Galloway, J. R.; Blumberg, J. B.; Ziegler, T. R. Plasma antioxidant status after high-dose chemotherapy: a randomized trial of parenteral nutrition in bone marrow transplantation patients. *Am J Clin Nutr* 72:181-189; 2000.

42. Jones, D. P. Redox potential of GSH/GSSG couple: assay and biological significance. *Methods Enzymol* 348:93-112; 2002.

43. Jones, D. P.; Carlson, J. L.; Samiec, P. S.; Sternberg, P., Jr.; Mody, V. C., Jr.; Reed, R. L.; Brown, L. A. Glutathione measurement in human plasma. Evaluation of sample collection, storage and derivatization conditions for analysis of dansyl derivatives by HPLC. *Clin Chim Acta* 275:175-184; 1998.

44. Jones, D. P.; Mody, V. C., Jr.; Carlson, J. L.; Lynn, M. J.; Sternberg, P., Jr. Redox analysis of human plasma allows separation of pro-oxidant events of aging from decline in antioxidant defenses. *Free Radic Biol Med* 33:1290-1300; 2002.

45. Kannel, W. B.; Wolf, P. A.; Benjamin, E. J.; Levy, D. Prevalence, incidence, prognosis, and predisposing conditions for atrial fibrillation: population-based estimates. *Am J Cardiol* 82:2 N-9N; 1998.

46. Khairallah, F.; Ezzedine, R.; Ganz, L. I.; London, B.; Saba, S. Epidemiology and determinants of outcome of admissions for atrial fibrillation in the United States from 1996 to 2001. *Am J Cardiol* 94:500-504; 2004.

47. Kim, Y. M.; Guzik, T. J.; Zhang, Y. H.; Zhang, M. H.; Kattach, H.; Ratnatunga, C.; Pillai, R.; Channon, K. M.; Casadei, B. A myocardial Nox2 containing NAD(P)H oxidase contributes to oxidative stress in human atrial fibrillation. *Circ Res* 97:629-636; 2005.

48. Kinnula, V. L. Focus on antioxidant enzymes and antioxidant strategies in smoking related airway diseases. *Thorax* 60:693-700; 2005.

49. Korantzopoulos, P.; Kolettis, T. M.; Kountouris, E.; Dimitroula, V.; Karanikis, P.; Pappa, E.; Siogas, K.; Goudevenos, J. A. Oral vitamin C administration reduces early recurrence rates after electrical cardioversion of persistent atrial fibrillation and attenuates associated inflammation. *Int J Cardiol* 102:321-326; 2005.

50. Korantzopoulos, P.; Kolettis, T. M.; Kountouris, E.; Siogas, K.; Goudevenos, J. A. Variation of inflammatory indexes after electrical cardioversion of persistent atrial fibrillation. Is there an association with early recurrence rates? *Int J Clin Pract* 59:881-885; 2005.

51. Kumagai, K.; Nakashima, H.; Saku, K. The HMG-CoA reductase inhibitor atorvastatin prevents atrial fibrillation by inhibiting inflammation in a canine sterile pericarditis model. *Cardiovasc Res* 62:105-111; 2004.

52. Lloyd-Jones, D. M.; Wang, T. J.; Leip, E. P.; Larson, M. G.; Levy, D.; Vasan, R. S.; D'Agostino, R. B.; Massaro, J.

M.; Beiser, A.; Wolf, P. A.; Benjamin, E. J. Lifetime risk for development of atrial fibrillation: the Framingham Heart Study. *Circulation* 110:1042-1046; 2004.

53. Lo, B.; Fijnheer, R.; Nierich, A. P.; Bruins, P.; Kalkman, C. J. C-reactive protein is a risk indicator for atrial fibrillation after myocardial revascularization. *Ann Thorac Surg* 79:1530-1535; 2005.

54. Malouf, J. F.; Kanagala, R.; Al Atawi, F. O.; Rosales, A. G.; Davison, D. E.; Murali, N. S.; Tsang, T. S.; Chandrasekaran, K.; Ammash, N. M.; Friedman, P. A.; Somers, V. K. High sensitivity C-reactive protein: a novel predictor for recurrence of atrial fibrillation after successful cardioversion. *J Am Coll Cardiol* 46:1284-1287; 2005.

55. Marin, F.; Pascual, D. A.; Roldan, V.; Arribas, J. M.; Ahumada, M.; Tornel, P. L.; Oliver, C.; Gomez-Plana, J.; Lip, G. Y.; Valdes, M. Statins and postoperative risk of atrial fibrillation following coronary artery bypass grafting. *Am J Cardiol* 97:55-60; 2006.

56. Mathew, J. P.; Fontes, M. L.; Tudor, I. C.; Ramsay, J.; Duke, P.; Mazer, C. D.; Barash, P. G.; Hsu, P. H.; Mangano, D. T. A multicenter risk index for atrial fibrillation after cardiac surgery. *JAMA* 291:1720-1729; 2004.

57. Mihm, M. J.; Yu, F.; Carnes, C. A.; Reiser, P. J.; McCarthy, P. M.; Van Wagoner, D. R.; Bauer, J. A. Impaired myofibrillar energetics and oxidative injury during human atrial fibrillation. *Circulation* 104:174-180; 2001.

58. Moriarty, S. E.; Shah, J. H.; Lynn, M.; Jiang, S.; Openo, K.; Jones, D. P.; Sternberg, P. Oxidation of glutathione and cysteine in human plasma associated with smoking. *Free Radic Biol Med* 35:1582-1588; 2003.

59. Mozaffarian, D.; Psaty, B. M.; Rimm, E. B.; Lemaitre, R. N.; Burke, G. L.; Lyles, M. F.; Lefkowitz, D.; Siscovick, D. S. Fish intake and risk of incident atrial fibrillation. *Circulation* 110:368-373; 2004.

60. Ozaydin, M.; Varol, E.; Aslan, S. M.; Kucuktepe, Z.; Dogan, A.; Ozturk, M.; Altinbas, A. Effect of atorvastatin on the recurrence rates of atrial fibrillation after electrical cardioversion. *Am J Cardiol* 97:1490-1493; 2006.

61. Pike, G. K.; Bretag, A. H.; Roberts, M. L. Modification of the transient outward current of rat atrial myocytes by metabolic inhibition and oxidant stress. *J Physiol* 470:365-382; 1993.

62. Prasongsukarn, K.; Abel, J. G.; Jamieson, W. R.; Cheung, A.; Russell, J. A.; Walley, K. R.; Lichtenstein, S. V. The effects of steroids on the occurrence of postoperative atrial fibrillation after coronary artery bypass grafting surgery: a prospective randomized trial. *J Thorac Cardiovasc Surg* 130:93-98; 2005.

63. Rahman, I.; MacNee, W. Role of oxidants/antioxidants in smoking-induced lung diseases. *Free Radic Biol Med* 21:669-681; 1996.

64. Rost, J.; Rapoport, S. Reduction potential of glutathione. *Nature* 201:185; 1964.

65. Samiec, P. S.; Drews-Botsch, C.; Flagg, E. W.; Kurtz, J. C.; Sternberg, P., Jr.; Reed, R. L.; Jones, D. P. Glutathione in human plasma: decline in association with aging, age-related macular degeneration, and diabetes. *Free Radic Biol Med* 24:699-704; 1998.

66. Schafer, F. Q.; Buettner, G. R. Redox environment of the cell as viewed through the redox state of the glutathione disulfide/glutathione couple. *Free Radic Biol Med* 30:1191-1212; 2001.

67. Shang, L. L.; Dudley, S. C., Jr. Tandem promoters and developmentally regulated 5' and 3' mRNA untranslated regions of the mouse scn5a cardiac sodium channel. *J Biol Chem* 280:933-940; 2005.

68. Shiroshita-Takeshita, A.; Brundel, B. J.; Lavoie, J.; Nattel, S. Prednisone prevents atrial fibrillation promotion by atrial tachycardia remodeling in dogs. *Cardiovasc Res* 69:865-875; 2006.

69. Shiroshita-Takeshita, A.; Schram, G.; Lavoie, J.; Nattel, S. Effect of simvastatin and antioxidant vitamins on atrial fibrillation promotion by atrial-tachycardia remodeling in dogs. *Circulation* 110:2313-2319; 2004.

70. Touyz, R. M.; Schiffrin, E. L. Reactive oxygen species in vascular biology: implications in hypertension. *Histochem Cell Biol* 122:339-352; 2004.

71. Tsubouchi, H.; Inoguchi, T.; Sonta, T.; Sato, N.; Sekiguchi, N.; Kobayashi, K.; Sumimoto, H.; Utsumi, H.; Nawata, H. Statin attenuates high glucose-induced and diabetes-induced oxidative stress in vitro and in vivo evaluated by electron spin resonance measurement. *Free Radic Biol Med* 39:444-452; 2005.

72. Vecchione, C.; Brandes, R. P. Withdrawal of 3-hydroxy-3-methylglutaryl coenzyme A reductase inhibitors elicits oxidative stress and induces endothelial dysfunction in mice. *Circ Res* 91:173-179; 2002.

73. Wagner, A. H.; Kohler, T.; Ruckschloss, U.; Just, I.; Hecker, M. Improvement of nitric oxide-dependent vasodilatation by HMG-CoA reductase inhibitors through attenuation of endothelial superoxide anion formation. *Arterioscler Thromb Vasc Biol* 20:61-69; 2000.

74. Wassmann, S.; Laufs, U.; Muller, K.; Konkol, C.; Ahlbory, K.; Baumer, A. T.; Linz, W.; Bohm, M.; Nickenig, G. Cellular antioxidant effects of atorvastatin in vitro and in vivo. *Arterioscler Thromb Vasc Biol* 22:300-305; 2002.

75. Watanabe, E.; Arakawa, T.; Uchiyama, T.; Kodama, I.; Hishida, H. High-sensitivity C-reactive protein is predictive of successful cardioversion for atrial fibrillation and maintenance of sinus rhythm after conversion. *Int J Cardiol* 108:346-353; 2006.

76. Yared, J. P.; Starr, N. J.; Torres, F. K.; Bashour, C. A.; Bourdakos, G.; Piedmonte, M.; Michener, J. A.; Davis, J. A.; Rosenberger, T. E. Effects of single dose, postinduction dexamethasone on recovery after cardiac surgery. *Ann Thorac Surg* 69:1420-1424; 2000.

77. Zarauza, J.; Rodriguez Lera, M. J.; Farinas, A. C.; Hernando, J. P.; Ceballos, B.; Gutierrez, B.; Perez, J.; Cuesta, J. M. Relationship Between C-Reactive Protein Level and Early Recurrence of Atrial Fibrillation After Electrical Cardioversion. *Rev Esp Cardiol* 59:125-129; 2006.

78. Neuman, R. B.; Bloom, H. L.; Shukrullah, I.; Darrow, L. A.; Kleinbaum, D.; Jones, D. P.; Dudley, Jr. S. C. Oxidative Stress Markers Are Associated with Persistent Atrial Fibrillation. *Clinical Chemistry* 53:9; published online Jun. 28, 2007, pp. 1-7.

79. Neuman, R. B.; Bloom, H. L.; Darrow, L. A.; Kleinbaum, D.; Dudley, Jr. S. C. Oxidative stress but not inflammatory markers predict presistent atrial fibrillation. Heart Rhythm Society Meeting, May 20, 2006. Abstract (1 page).

What is claimed is:

1. A method of predicting onset or risk of atrial fibrillation (AF) in a subject, comprising:
    determining the presence of an oxidative stress marker in a biological sample taken from a subject, wherein the presence of the oxidative stress marker in the biological sample serves to predict the onset or risk of atrial fibrillation in the subject.

2. The method of claim 1, wherein:
    the presence of the oxidative stress marker is indicated by an abnormal thiol ratio for at least one member selected from the group consisting of glutathione, cysteine, and a combination thereof.

3. The method of claim 2, wherein:
the abnormal thiol ratio represents a higher than a predetermined normal oxidized state value for the selected marker.

4. The method of claim 3, wherein:
the normal oxidized state value comprises median values of −143 mV and −67 mV for glutathione and cysteine, respectively.

5. The method of claim 4, wherein:
a change in the median value of 15 mV corresponds to about four-fold increase for the onset of atrial fibrillation.

6. The method of claim 1, wherein:
the presence of the oxidative stress marker is indicated by an abnormal oxidized state of a derivative of a reactive oxidative metabolite (DROM).

7. The method of claim 6, wherein:
the abnormal oxidized state represents a higher than a predetermined normal oxidized state value for the derivative.

8. The method of claim 7, wherein:
the normal oxidized state value comprises a median value of 370 Carr units.

9. The method of claim 1, wherein:
the biological sample comprises human blood.

10. A method for treating a subject suspect of having atrial fibrillation, comprising:
   a) determining the presence of an elevated blood level of an oxidative stress marker;
   b) comparing the value obtained in step a) to a predetermined normal value;
   c) determining the onset or risk of atrial fibrillation in the subject if the value obtained in step a) is higher than the normal value; and
   d) recommending the subject for an antioxidant therapy if the onset or risk of atrial fibrillation in the subject is determined.

11. The method of claim 10, wherein:
the oxidative stress marker comprises at least one member selected from the group consisting of glutathione, cysteine, and a combination thereof.

12. The method of claim 10, wherein:
the oxidative stress marker comprises a derivative of a reactive oxidative metabolite (DROM).

13. The method of claim 10, wherein:
the antioxidant comprises a statin.

14. A method for predicting onset or risk of atrial fibrillation (AF) in a subject, comprising:
determining the presence of an oxidative stress marker in a biological sample taken from a subject, wherein the presence of the oxidative stress marker in the biological sample serves to predict the onset or risk of atrial fibrillation in the subject; and
wherein the stress marker comprises at least one member selected from the group consisting of glutathione, cysteine, a derivative of a reactive oxidative metabolic (DROM), and a combination thereof.

15. The method of claim 14, wherein:
the biological sample comprises human blood.

* * * * *